(12) United States Patent
Yamamoto (10) Patent No.: US 8,733,415 B2
(45) Date of Patent: May 27, 2014

(54) APPARATUS FOR MANUFACTURING ABSORBENT ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 379 days.

(21) Appl. No.: 12/715,973

(22) Filed: Mar. 2, 2010

(65) Prior Publication Data

US 2010/0175807 A1    Jul. 15, 2010

(30) Foreign Application Priority Data

Mar. 2, 2009    (JP) ................................ P2009-048652

(51) Int. Cl.
    *A61F 13/15*    (2006.01)
(52) U.S. Cl.
    USPC .......................................... 156/362; 156/440
(58) Field of Classification Search
    None
    See application file for complete search history.

(56) References Cited

U.S. PATENT DOCUMENTS

| | | | |
|---|---|---|---|
| 5,693,165 A * | 12/1997 | Schmitz | 156/164 |
| 5,779,689 A | 7/1998 | Pfeifer | |
| 6,505,791 B1 | 1/2003 | Syndikus et al. | |
| 7,045,031 B2 | 5/2006 | Popp et al. | |
| 2006/0185135 A1* | 8/2006 | Yamamoto et al. | 28/116 |
| 2010/0078127 A1* | 4/2010 | Yamamoto et al. | 156/306.3 |

FOREIGN PATENT DOCUMENTS

| | | |
|---|---|---|
| EP | 1260203 A2 | 11/2002 |
| EP | 2356960 A1 | 8/2011 |
| JP | 03-033201 A | 2/1991 |
| JP | 6502091 A | 3/1994 |
| JP | 6-327716 A | 11/1994 |
| JP | 9-564 A | 9/1997 |
| JP | 2001346825 A | 12/2001 |
| JP | 2004-159866 A | 6/2004 |
| JP | 2004159866 A | 6/2004 |
| JP | 2006-141642 A | 6/2006 |
| JP | 2010-115282 A | 5/2010 |
| JP | 2010-115284 A | 5/2010 |
| WO | 9207531 A1 | 5/1992 |
| WO | 9965810 A1 | 12/1999 |

OTHER PUBLICATIONS

International Search Report and Written Opinion issued on Jul. 20, 2010 in the counterpart PCT Patent Application.
Office Action issued Apr. 15, 2013 corresponds to Chilean patent application No. 2011-002138.
Office Action mailed Apr. 26, 2013 corresponds to Chinese patent application No. 201080010396.8.

(Continued)

*Primary Examiner* — Barbara J Musser
(74) *Attorney, Agent, or Firm* — Lowe Hauptman & Ham LLP (57) ABSTRACT

An apparatus for manufacturing an absorbent article includes an arm member having a tip end portion feeding the elastic member. The tip end portion moves alternately in a first direction and a second direction, so that the elastic member is brought into contact with a web being conveyed in a predetermined direction with a continuum of components constituting one portion of the absorbent article and is placed in a predetermined waveform. Here, in a plan view of the web, a distance between the arm member and a nip point becomes largest when the nip point goes beyond a position on the predetermined waveform where an angle between the predetermined direction and a tangent line to the predetermined waveform becomes largest.

14 Claims, 7 Drawing Sheets

(56) References Cited

OTHER PUBLICATIONS

Office Action issued May 14, 2013 corresponds to Colombian patent application No. 11-122080.
Extended European Search Report dated Sep. 30, 2013, corresponds to European patent application No. 10748870.2.
Office Action issued Jan. 22, 2013 corresponds to Mexican patent application No. MX/a/2010/002489.
Office Action issued Jul. 25, 2013 corresponds to Mexican patent application No. MX/a/2010/002489.
Office Action mailed Aug. 28, 2013 corresponds to Egyptian patent application No. 1469/2011.

* cited by examiner

APPARATUS FOR MANUFACTURING ABSORBENT ARTICLE

TECHNICAL FIELD

The present disclosure relates to an apparatus and a method of manufacturing an absorbent article in which a guide unit configured to guide an elastic member is used to place the elastic member on a web being conveyed in a predetermined direction with a continuum of components constituting one portion of an absorbent article.

BACKGROUND ART

In the conventional process of manufacturing absorbent articles, such as disposable diapers, widely used is a method in which string-like elastic members (rubber) are arranged in portions to be processed into leg-surrounding regions and a crotch region which constitute an absorbent article so that the leg-surrounding regions and the crotch region should be more fitted to a person to wear the absorbent article (for example, a human body).

Specifically, in the manufacturing process, the string-like elastic members are placed in waveforms on a web with continua of components such as a back sheet and an absorption sheet to form absorbent articles. In other words, the string-like elastic members are placed in waveforms on the web conveyed by a crosswise conveyor system in which absorbent articles to be formed are arranged with a longitudinal direction of each of the absorbent articles going in a cross direction (a CD direction) which intersects a conveyance direction (an MD direction) of the web. In this way, the absorbent article having gathers to be fitted to the shapes of the leg-surrounding regions and the crotch region can be continuously formed.

As described above, as a method for placing string-like elastic members in waveforms on a web being conveyed, there is known a method in which a guide member guiding feeding positions of elastic members onto a web is driven by a cam (see Patent Literature 1, for example).

There is also known a method in which a guide member guiding feeding positions of elastic members onto a web is reciprocally moved in a cross direction intersecting a conveyance direction of the web (see Patent Literature 2, for example).

It is not realistic in terms of the layout of an apparatus to bring a guide member into contact with a nip point to align the nip point with the feeding position of a elastic member guided by the guide member. Here, the nip point is that at which an elastic member and a web are held between press rollers provided above and below the web and thereby come in contact with each other. For this reason, a certain distance is generally provided between the nip point and the feeding position. In other words, the distance has to be considered when the profile of a device moving the guide member is designed.

The inventors have discovered that, in the known technique, the aforementioned conventional apparatus for manufacturing an absorbent article has the following problem.

Specifically, to place an elastic member accurately in a desired position on a web being conveyed at high speed, the profile of a device such as a cam has to be elaborately designed in consideration of a distance between a nip point and a feeding position.

The present invention has been made in view of the foregoing circumstances. Accordingly, an object of the present invention is to provide an apparatus and a method of manufacturing an absorbent article that are capable of placing a elastic member in a desired position on a web being conveyed at high speed without elaborate profile designing.

CITATION LIST

Patent Literatures

PTL 1. Japanese Patent Application Publication No. Hei 3-33201 (p. 4, FIGS. 6 and 7)
PTL 2. Japanese Patent Application Publication No. 2006-141642 (p. 10, FIG. 1)

SUMMARY

To solve the above-described problem, the present invention has the following aspects.

In a aspect of the present invention provides an apparatus for manufacturing an absorbent article, the apparatus including a guide unit that has a feeding part configured to feed a elastic member and that is configured to guide the elastic member, the guide unit moving the feeding part alternately in a first direction and a second direction, so that the elastic member is brought into contact with a web being conveyed in a predetermined direction with a continuum of components constituting one portion of the absorbent article and is placed in a predetermined waveform, the first direction extending from a center portion of the web to a first end portion in a cross direction intersecting the predetermined direction, the second direction extending from the center portion to a second end portion opposite to the first end portion, the apparatus comprising a speed controller configured to control a speed of the elastic member which is fed from the feeding part, wherein the speed controller maintains the speed of the elastic member in a constant speed different from a conveyance velocity of the web being conveyed in the predetermined direction, and in a plan view of the web, a distance between the feeding part and a nip point where the elastic member is brought into contact with the web becomes largest when the nip point goes beyond a position on the predetermined waveform where an angle between the predetermined direction and a tangent line to the predetermined waveform becomes largest.

According to the aspect of the present invention, there can be provided an apparatus and a method of manufacturing an absorbent article that are capable of easily placing a elastic member in a desired position on a web being conveyed at high speed along a predetermined waveform.

DETAILED DESCRIPTION

Hereinafter, a conveyor and a method of manufacturing an absorbent article according to the present invention will be described with reference to the accompanying drawings.

Note that, in the following description of the drawings, same reference signs denote same elements and portions. In addition, it should be noted that the drawings are schematic and are not to scale unless otherwise specified.

Therefore, specific dimensions and the like should be determined by taking the following description into consideration. Moreover, the drawings do not necessarily reflect the real-life dimensional relationships and ratios of components.

Figure 1:
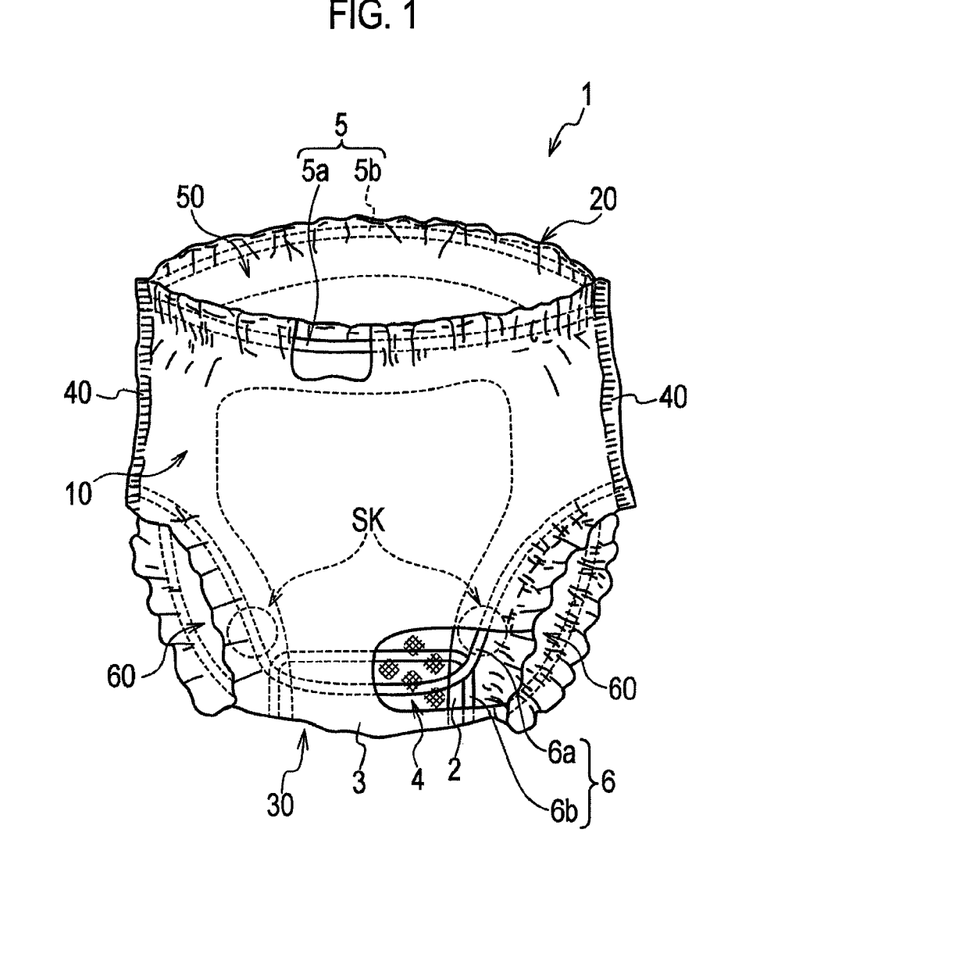
FIG. 1 is a perspective view showing an absorbent article according to one or more embodiments.

In the first place, a configuration of an absorbent article according to an embodiment will be explained with reference to the drawing. FIG. 1 is a perspective view showing the absorbent article 1 according to one or more embodiments. In the particularly illustrated embodiment, the absorbent article 1 is a disposable pants-type diaper for adults.

As shown in FIG. 1, the absorbent article 1 substantially includes a liquid-permeable top sheet 2, a back sheet 3, and an absorber 4.

The top sheet 2 is to come in contact with the skin of a person to wear the absorbent article 1 (hereinafter, called a "wearer"). The back sheet 3 is provided outside the top sheet 2. The absorber 4 is provided between the top sheet 2 and the back sheet 3, and absorbs excretion from the wearer.

Note that a liquid-impermeable waterproof sheet (unillustrated) is provided between the back sheet 3 and the absorber 4. In other words, the absorber 4 is provided between the top sheet 2 and the waterproof sheet.

The top sheet 2 is made of a nonwoven fabric or a perforated plastic film. The back sheet 3 is made of a nonwoven fabric. The absorber 4 is made of, for example, ground pulp or a mixture of ground pulp and superabsorbent polymer particles. The waterproof sheet is made of, for example, a plastic, a nonwoven fabric, or a mixed sheet of a plastic film and a nonwoven fabric.

The absorbent article 1 has a front waistline region 10 to be fitted to the front waist of a wearer, a back waistline region 20 to be fitted to the back waist of the wearer, and a crotch region 30 to be fitted to the crotch of the wearer.

The front waistline region 10 and the back waistline region 20 are joined together by joint portions 40. Waist gathers 5 made of a stretchable string-like rubber or the like are provided to an entire peripheral edge of the front waistline region 10 and the back waistline region 20. The waist gathers 5 include a front waist gather 5a which is positioned in the front waistline region 10 and a back waist gather 5b which is positioned in the back waistline region 20. In addition, a waist opening region 50 is formed between the front waist gather 5a and the back waist gather 5b.

Figure 2:
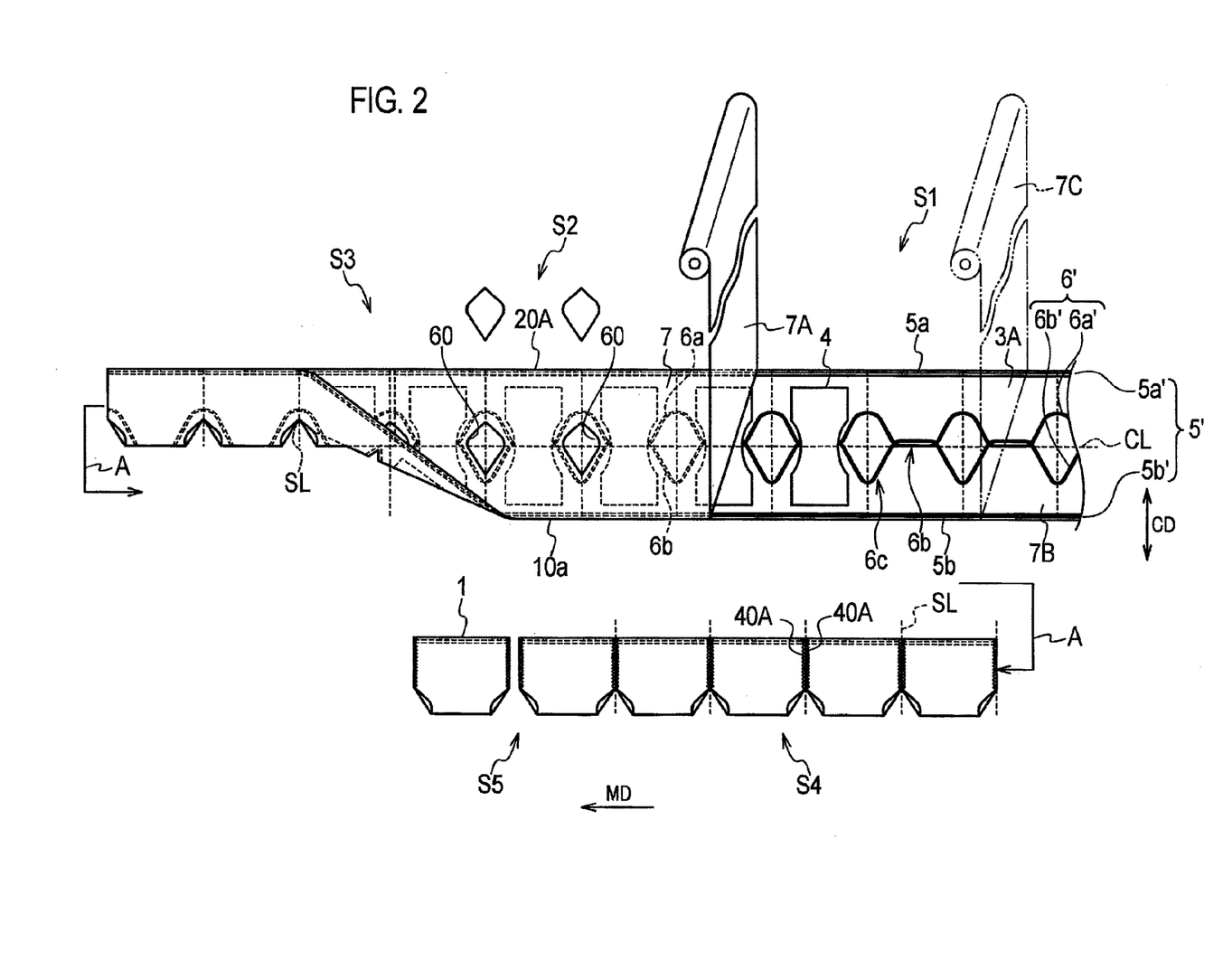
FIG. 2 is a view for illustrating part of a method of manufacturing an absorbent article according to one or more embodiments.

The front waistline region 10 and the back waistline region 20 are stretchable in the conveyance direction MD (the MD direction) of a first web 7A constituting the top sheet 2 and a second web 73 constituting the back surface sheet 3 (see FIG. 2). For example, to make the front waistline region 10 and the back waistline region 20 stretchable in the conveyance direction, MD, the front waistline region 10 and the back waistline region 20 may be provided with the waist gathers 5 or may themselves be made of a stretchable sheet from the beginning.

The crotch region 30 is provided between the front waistline region 10 and the back waistline region 20. Leg gathers 6 made of a stretchable string-like rubber or the like are provided on both sides of the crotch region 30. Each of the leg gathers 6 includes a front leg gather 6a positioned close to the front waistline region 10 and a back leg gather 6b positioned close to the back waistline region 20. A leg-surrounding openings 60 is formed between the front leg gather 6a and the back leg gather 6b and on each side of the crotch regions 30.

The crotch region 30 is stretchable in the cross direction CD (the CD direction) intersecting the conveyance direction MD of the web. For example, to make the crotch region 30 stretchable in the cross direction CD, the crotch region 30 may be provided with the leg gather 6, or may itself be made of a stretchable sheet from the beginning.

In FIG. 1, regions Sk show portions to be fitted to the inguinal regions of the wearer when the wearer wears the diaper. The details of a method for placing the front leg gather 6a in the region Sk will be described later.

Secondly, a configuration of a method of manufacturing an absorbent article according to this embodiment will be explained with reference to the drawing. FIG. 2 is a diagram for explaining part of the method of manufacturing an absorbent article according to this embodiment.

As shown in FIG. 2, the method of manufacturing an absorbent article includes at least a component placing step, a leg-surrounding forming step, a folding step, a joining step and a cutting step.

Note that, between each two of the steps, performed is a conveying step using an unillustrated conveyor (e.g. a belt conveyor) of conveying the liquid-permeable first web 7A, the liquid-impermeable second web 7B, and a third web 7C in the conveyance direction MD (a predetermined direction). The liquid-permeable first web 7A constitutes the top sheet 2, the liquid-impermeable second web 7B constitutes the back sheet 3, and a third web 7C is made of, for example, the same material as that of the second web 7B and constitutes the back sheet 3.

In the component placing step S1, components to constitute the absorbent article 1, such as the elastic member, the third web 7C, the waterproof sheet (unillustrated), and the absorber 4, are placed on the second web 7B.

Specifically, in the first place, elastic members 5' constituting the waist gathers 5 are linearly placed in a stretched state in portions corresponding to the front waistline region 10 and the back waistline region 20 on the second web 7B. In other words, a elastic member 5a' constituting the front waist gather 5a and a elastic member 5b' constituting the back waist gather 5b are placed in portions corresponding to the front waistline region 10 and the back waistline region 20 on the second web 7B. Accordingly, the waist gathers 5 (the front waist gather 5a and the back waist gather 5b) are formed in the portions corresponding to the front waistline region 10 and the back waistline region 20 on the second web 7B.

Secondly, the third web 7C is placed on the second web 7B. At the same time, in portions corresponding to the crotch regions 30 on the second web 7B and the third web 7C, the elastic members 6' constituting the leg gathers 6 are placed in a stretched state while swinging in the cross direction CD at predetermined cycles. After that, the elastic members 6' are held between the second web 7B and the third web 7C to form the leg gathers 6 (the front leg gather 6a and the back leg gather 6b).

Note that the second web 7B and the third web 7C holding the elastic members 6' therebetween are pressed by an upper press roll 130A and a lower press roll 130B.

The elastic member 6a' constituting the front leg gather 6a and the elastic member 6b' constituting the back leg gather 6b form a large ring portion 6c and a small ring portion 6d whose size in the cross direction CD is smaller than the large ring portion 6c.

As described above, the elastic members 6' are placed between the second web 7B and the third web 7C, and then the second web 7B and the third web 7C are pressed by the upper press roll 130A and the lower press roll 130B. If the position where the small ring portion 6d is supposed to be formed is not pressed, the elastic members 6' are not fixed in predetermined positions on the web. The elastic members 6' are placed in a stretched state, and thus are contracted to form substantially straight lines shifted from the predetermined forms placed, on the web in positions where the elastic members 6' are not fixed. In this manner, the small ring portion 6d is formed.

Similarly, this is applicable to the case where an adhesive is not applied to the predetermined positions. Specifically, the elastic members 6' are not fixed on the web in positions where an adhesive is not supposed to be applied, so that a small ring portion 6d is similarly formed.

Thirdly, the waterproof sheet (unillustrated) and the absorber 4 are placed on the second web 7B and the third web 7C holding the elastic members 6' therebetween so as to be arranged in the conveyance direction MD at regular intervals. Note that the waterproof sheet may be placed on the second web 7B and the third web 7C with the absorber 4 being joined therewith in advance or may be placed on the second web 7B and the third web 7C with the absorber 4 being separated therefrom.

Fourthly, the first web 7A constituting the top sheet 2 is placed on the second web 7B and the third web 7C on which the components constituting the absorbent article 1 are placed.

Note that, in the component placing step S1, the order from first to fourth is not necessarily required and may be changed as needed.

In the leg-surrounding forming step S2, leg-surrounding openings 60 (so-called leg holes) are formed after the component placing step S1 by cutting, along the internal circumference of the large ring portion 6c, the second web 7B and the first web 7A (hereinafter referred to as a composite web 7) which hold the components therebetween.

In the folding step S3, the composite web 7 is folded into two parts, after the leg-surrounding forming step S2, along the center line CL extending in the conveyance direction MD through the center of the cross direction CD of the composite web 7. In other words, a side edge 10A of the composite web 7 which corresponds to the front waistline region 10 and a side edge 20A of the composite web 7 which corresponds to the back waistline region 20 are placed one upon another in a state of matching each other.

In the joining step S4 after the folding step S3, the two folded parts of the web 7 are joined together through ultrasonic treatment or heat treatment at predetermined regions 40A corresponding to the joint portions 40 of the absorbent article 1. The predetermined region 40A is a region on both sides, in the conveyance direction MD, of an phantom line SL indicating a to-be-cut position extending in the cross direction CD of the web.

In the cutting step S5, the composite web 7 with the two folded parts joined at the predetermined regions 40A is cut along the phantom lines SL after the joining step S4. Thereby, the absorbent article 1 is manufactured.

Figure 3:
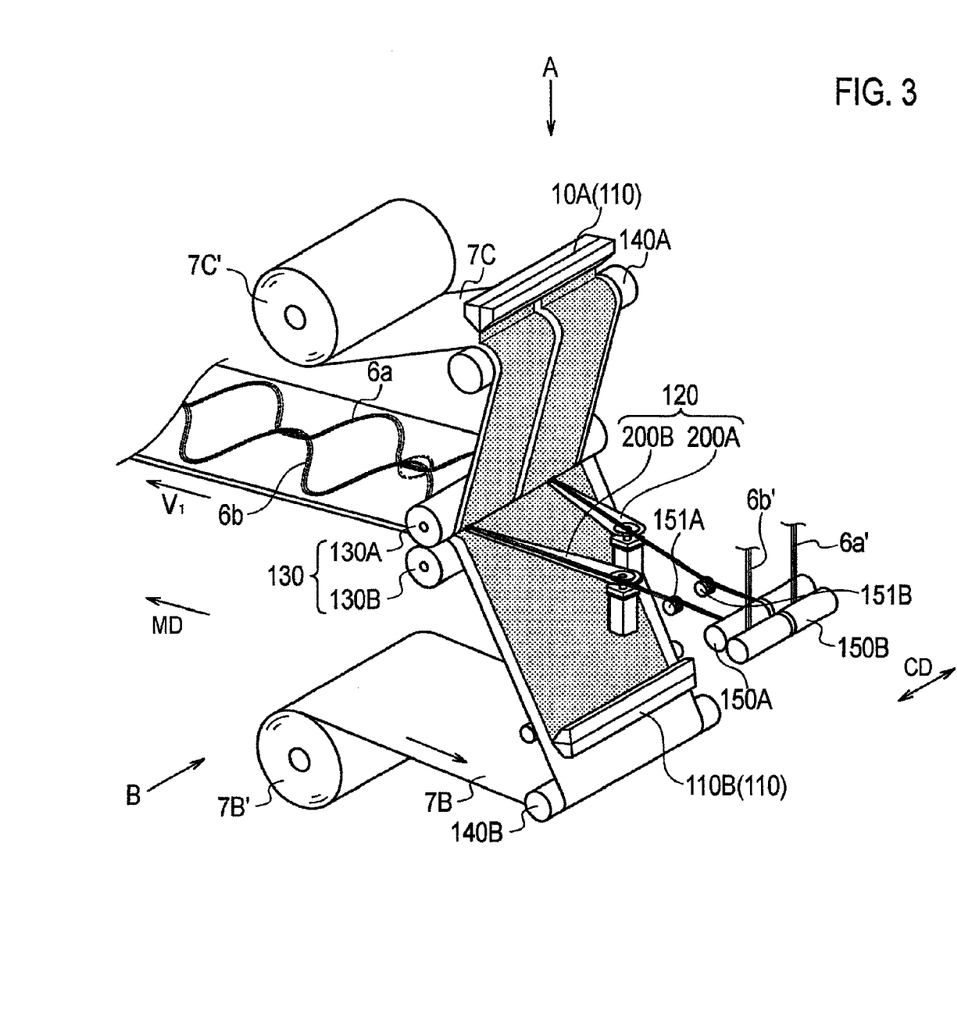
FIG. 3 is a perspective view showing an elastic member attaching apparatus according to one or more embodiments.
Figure 4:
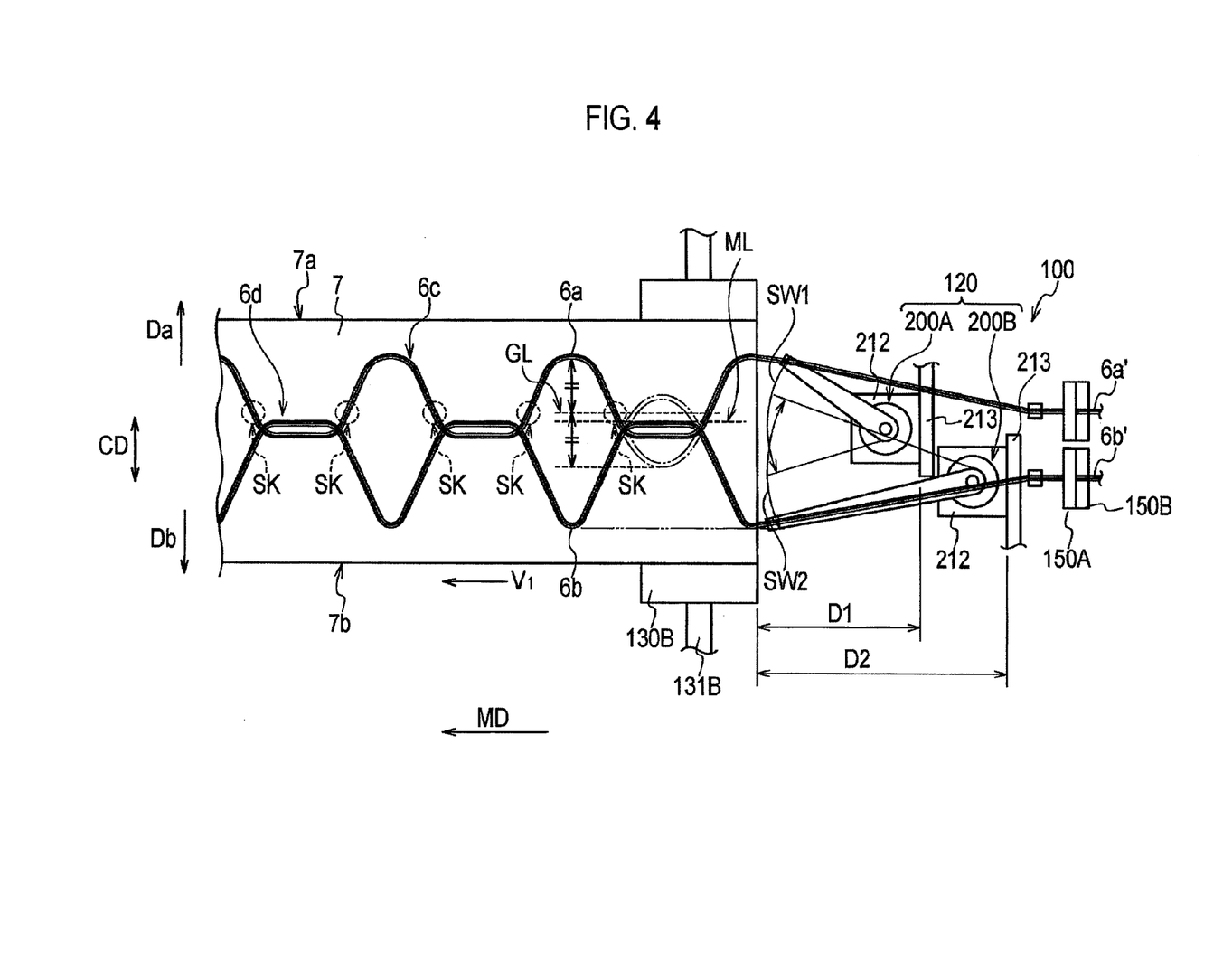
FIG. 4 is a top view (a view on arrow A in FIG. 3) showing the elastic member attaching apparatus according to one or more embodiments.
Figure 5:
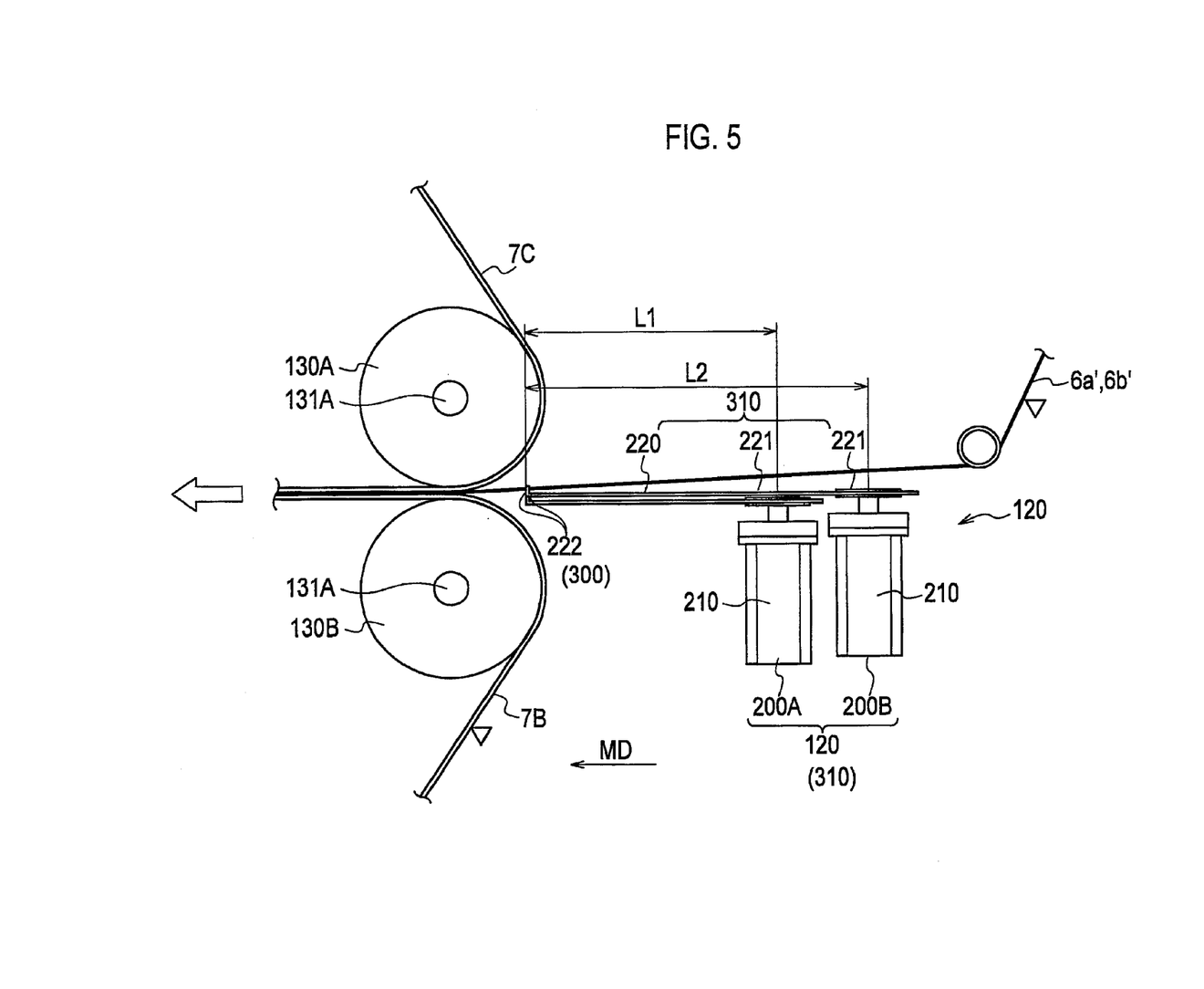
FIG. 5 is a side view (a view on arrow B in FIG. 3) showing the elastic member attaching apparatus according to one or more embodiments.

Hereinafter, the configuration of a elastic member attaching apparatus (an apparatus for manufacturing an absorbent article) used in the above-described component attaching step is described with reference to the drawings. FIG. 3 is a perspective view showing the elastic member attaching apparatus according to the embodiment. FIG. 4 is a top view (a view on arrow A in FIG. 3) showing the elastic member attaching apparatus according to the embodiment. FIG. 5 is a side view (a view on arrow B in FIG. 3) showing the elastic member attaching apparatus according to the embodiment.

As shown in FIGS. 3 to 5, the elastic member attaching apparatus 100 places the elastic members 6' constituting the leg gathers 6 between the second web 7B and the third web 7C by causing the elastic members 6' to swing in the cross direction CD at predetermined cycles. In other words, the elastic member attaching apparatus 100 places the elastic members 6' in a curved state between the second web 7B and the third web 7C, so that the leg gathers 6 (the front leg gather 6a and the back leg gather 6b) are formed.

Figure 7:
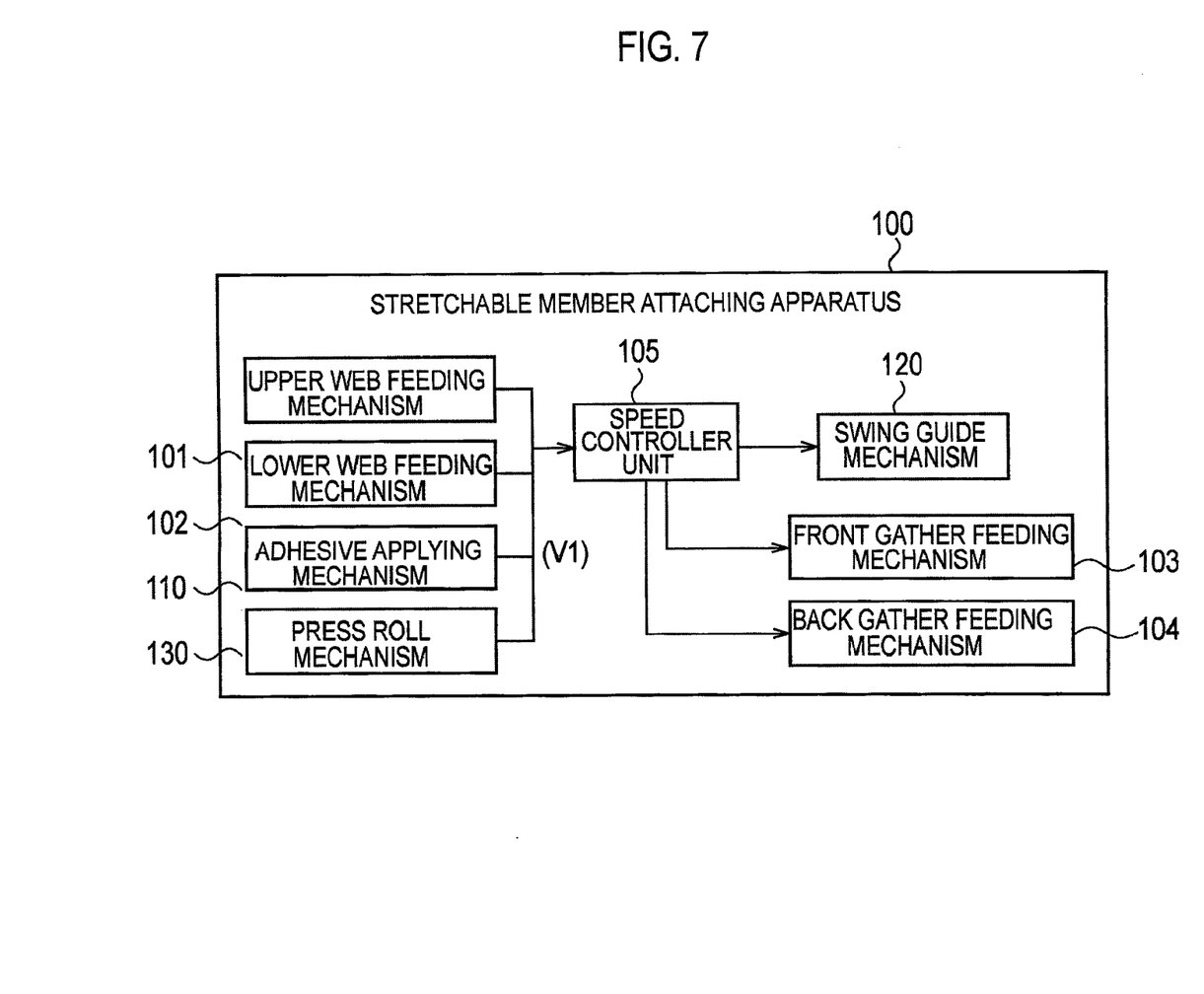
FIG. 7 is a block diagram showing the configuration of the elastic member attaching apparatus according to one or more embodiments.

FIG. 7 is a block diagram for illustrating the configuration of the elastic member attaching apparatus 100. The elastic member attaching apparatus 100 at least includes upper web feeding mechanism 101 and lower web feeding mechanism 102 (unillustrated in FIG. 3 and see FIG. 7), gather feeding mechanisms 103 and 104 (unillustrated in FIG. 3 and see FIG. 7), an applying mechanism 110, a swing guide mechanism 120 (a guide arm unit), and a press roll mechanism 130.

The web feeding mechanisms continuously feeds the webs respectively from web rolls. Specifically, the web feeding mechanisms include an upper web feeding mechanism 101 continuously feeding the third web 7C from a third web roll 7C' and a lower web feeding mechanism 102 continuously feeding the second web 7B from a second web roll 7B'.

The upper web feeding mechanism 101 and the lower web feeding mechanism 102 continuously feed the second web 7B and the third web 7C toward the press roll mechanism 130 respectively through rollers 140A and 140B rotating about a rotation axis (unillustrated) in the cross direction CD.

The gather feeding mechanisms continuously feed the elastic members 6' constituting the leg gathers 6 respectively from web rolls. Specifically, the gather feeding mechanisms include a front gather feeding mechanism 103 continuously feeding the elastic member 6a' constituting the front leg gather 6a from the corresponding web roll (unillustrated) and a back gather feeding mechanism 104 continuously feeding the elastic member 6b' constituting the back leg gather 6b from the corresponding web roll (unillustrated).

The front gather feeding mechanism 103 and the back gather feeding mechanism 104 continuously feed the leg gathers 6 toward the press roll mechanism 130 respectively through feed rolls 150A and 150B which rotate about the rotation axis in the cross direction CD and through branch rolls 151A and 151B which respectively separate the elastic member 6a' and the elastic member 6b' into strings.

As shown in FIG. 7, the elastic member attaching apparatus 100 has a speed controller 105 configured to control a speed of feeding the front leg gather 6a from the front gather feeding mechanism 103 and a speed of feeding the back leg gather 6b from the back gather feeding mechanism 104. The speed controller 105 maintains the speed of feeding the elastic member 6a' constituting the front leg gather 6a and being fed from the front gather feeding mechanism 103 in a constant speed different from a conveyance velocity (V1) of the web. Also, the speed controller maintains the speed of feeding the elastic member 6B' constituting the back leg gather 6b and being fed from the back gather feeding mechanism 104 in a constant speed different from the conveyance velocity (V1) of the web.

Specifically, the speed controller 105 maintains the speeds of feeding the elastic members 6a' and 6b' in a constant speed lower than the conveyance velocity (V1) of the web. Also, the speed controller 105 controls a servomotor (to be described later) in the swing guide mechanism 120.

The adhesive applying mechanism 110 is a spraying device applying an adhesive (e.g. a hot melt adhesive) onto the web. Specifically, the adhesive applying mechanism 110 has an upper adhesive applying mechanism 110A applying an adhesive onto the third web 7C and a lower adhesive applying mechanism 110B applying an adhesive onto the second web 7B.

Note that the upper adhesive applying mechanism 110A applies an adhesive onto a surface of the third web 7C other than the center portion thereof. In contrast, the lower adhesive applying mechanism 110B applies an adhesive onto an entire surface of the second web 7B.

The swing guide mechanism 120 causes the elastic members 6' constituting the leg gathers 6 to swing at predetermined cycles in the cross direction CD. The swing guide mechanism 120 has a first swing guide mechanism 200A causing the elastic member 6a' constituting the front leg gather 6a to swing and a second swing guide member 200B causing the elastic member 6b' constituting the back leg gather 6b to swing. The detail of the swing guide mechanism 120 will be given later.

The press roll mechanism 130 presses the second web 7B and the third web 7C with the elastic members 6' being held between the second web 7B and the third web 7C. Specifically, the press roll mechanism 130 has an upper press roll 130A coming in contact with the third web 7C and a lower press roll 130B coming in contact with the second web 7B.

The upper press roll 130A rotates about a rotation axis 131A along the cross direction CD. Similarly, the lower press roll 130B rotates about a rotation axis 130B in the cross direction CD. The elastic members 6' are guided by the swing guide mechanism 120 to a position where the upper press roll 130A and the lower press roll 130B are closest to each other.

Hereinafter, the configuration of the swing guide mechanism 120 which is characteristic to the present invention is described with reference to FIGS. 3 to 5.

The first swing guide mechanism 200A and the second swing guide mechanism 200B have basically the same configuration except the lengths of arm members 220. This is described later. For this reason, the first swing guide mechanism 200A and the second swing guide mechanism 200B are collectively described as the swing guide mechanism 120.

As shown in FIGS. 3 to 5, the swing guide mechanism 120 includes a motor 210 having a pivot 211, an arm member 220 which guides the elastic member 6' to a predetermined position in the cross direction CD between the second web 7B and the third web 7C, the pivot 211, and a base end portion 221 of the arm member 220.

The motor 210 includes a servomotor which provides a predetermined extent of a stretching magnification to the elastic member 6' according to the conveyance velocity (V1) of the web and which is operated by a controller programmed to be capable of placing the elastic member 6' in a desired layout.

Note that a program to operate the motor 210 of the first swing guide mechanism 200A is different from a program to operate the motor 210 of the second swing guide mechanism 200B. In other words, the predetermined stretching magnification and layout in the front leg gather 6a are different from those of the back leg gather 6b.

The motor 210 is attached to a base plate 213 through a bracket 212 (see FIG. 4). The motor 210 is configured so that the position thereof on the base plate 213 may be movable in the cross direction CD as needed. Note that a distance D1 is different from a distance D2, where the distance D1 is a distance between the press roll mechanism 130 and the base plate 213 on which the motor 210 of the first swing guide mechanism 200A is attached, and the distance D2 is a distance between the press roll mechanism 130 and the base plate 213 on which the motor 210 of the second swing guide mechanism 200B is attached.

The arm member 220 has a plate shape which is gradually tapered from the base end portion 211 toward a tip end portion 222. It is preferable that the arm member 220 be horizontally placed (see FIG. 5).

The arm member 220 is made of a metal steel plate. For example, the arm member 220 is made of a stainless steel plate.

The tip end portion 222 of the arm member 220 is bent toward the side opposite to the side where the motor 210 is positioned with respect to the arm member 220. The tip end portion 222 of the arm member 220 has an insertion hole 223 into which the leg gather 6 is inserted.

In the present embodiment, the arm members 220 of the first swing guide mechanism 200A and the second swing guide mechanism 200B are different in length. The length L1 of the arm member 220 of the first swing guide mechanism 200A is larger than the length L2 of the arm member 220 of the second swing guide mechanism 200B. Meanwhile, the distances from the tip end portions 222 of the first swing guide mechanism 200A and the second swing guide mechanism 200B to the press roll mechanism 130 are equal to each other. Therefore, the relationship between the distance D1 and the distance D2 can be expressed by D2>D1.

Figure 6:
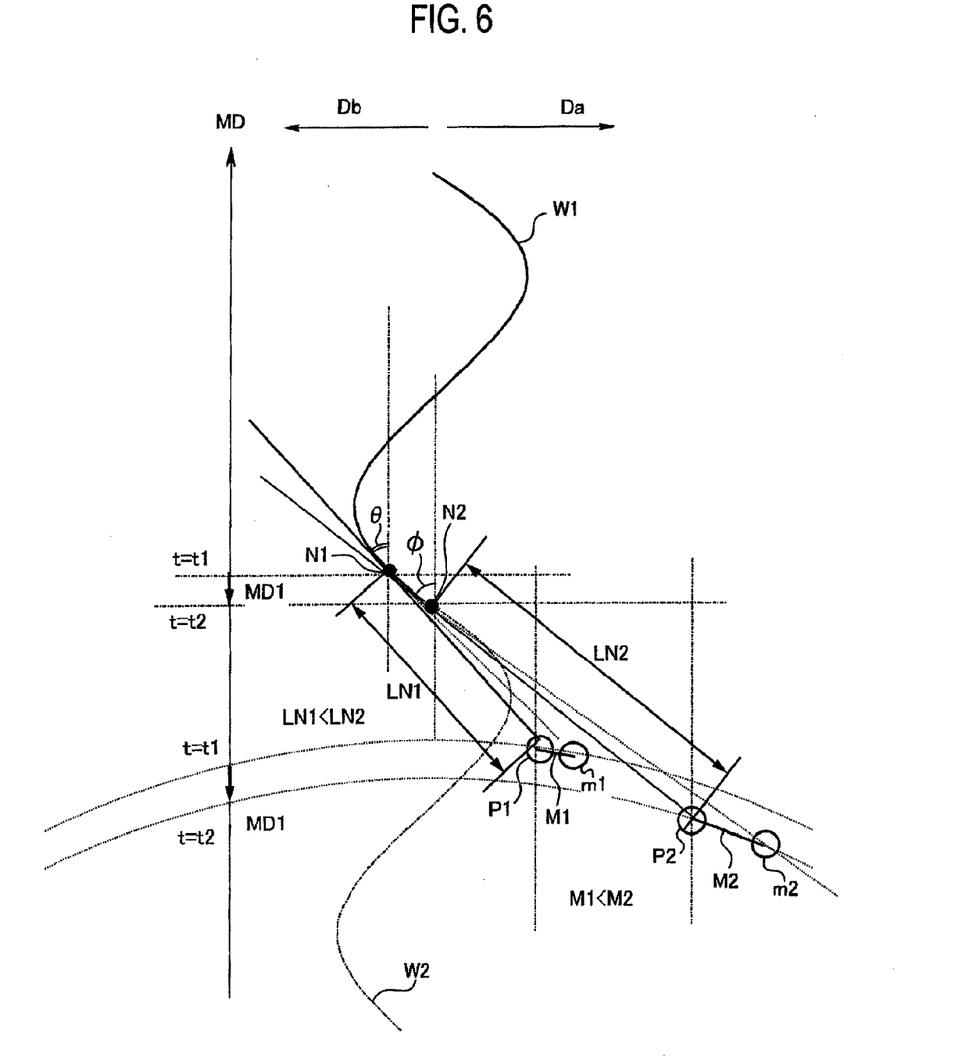
FIG. 6 is a schematic view showing how a front leg gather is placed in the top view (the view on arrow A in FIG. 3) shown in FIG. 4.

For example, the length L1 of the arm member 220 of the first swing guide mechanism 200A is 450 mm (see FIGS. 5 and 6). On the other hand, the length L2 of the arm member 220 of the second swing guide mechanism 200B is 600 mm (see FIGS. 5 and 6).

Note that the length of the arm member 220 means herein a length from the tip end portion 222 of the arm member 220 to the pivot 211 of the arm member 220.

A weight of the arm member 220 of the first swing guide mechanism 200A is 300 g, while a weight of the arm member 220 of the second swing guide mechanism 200B is 400 g.

An amplitude SW1 of the tip end portion 222 of the first swing guide mechanism 200A in the cross direction CD is 200 mm (see FIG. 4). On the other hand, an amplitude SW2 of the tip end portion 222 of the arm member 220 of the second swing guide mechanism 200B in the cross direction CD is 350 mm (see FIG. 4).

Hereinafter, the operation of the elastic member attaching apparatus 100 according to the embodiment is described with reference to FIGS. 3 to 5.

The upper web feeding mechanism feeds the third web 3C from a third web roll 7C', and the roller 140A changes the moving direction of the web. The upper adhesive applying mechanism 110A applies an adhesive onto the surface, facing the second web 7B, of the third web 7C whose moving direction is changed. At this time, the upper adhesive applying mechanism 110A applies the adhesive onto the surface of the third web 7C except the center portion thereof. The third web 7C onto which the adhesive is applied is supplied between the upper press roll 130A and the lower press roll 130B from above.

Similarly, the lower web feeding mechanism feeds the second web 7B from the second web roll 7B', and the roller 140B changes the moving direction of the web. The lower adhesive applying mechanism 110B applies the adhesive onto the surface, facing the third web 7C, of the second web 7B whose moving direction is changed. The second web 7B onto which the adhesive is applied is supplied between the upper press roll 130A and the lower press roll 130B from below.

The front gather feeding mechanism feeds the elastic member 6a' from the web roll (unillustrated), and the feed roll 150A turns the moving direction of the elastic member. The branch roll 151A separates into strings the elastic member 6a' turned by the feed roll 150A. The first swinging guide mechanism 200A causes the strings of the elastic member 6a' to swing at predetermined cycles in the cross direction CD. Accordingly, the elastic member 6a' is placed in a curved state between the second web 7B and the third web 7C, so that the front leg gather 6a is formed.

Similarly, the back gather feeding mechanism feeds the elastic member 6b' from the web roll (unillustrated), and the feed roll 150B turns the moving direction of the elastic member 6b'. The branch roll 151B separates into strings the elastic member 6b' which is turned by the feed roll 150B. The second swinging guide mechanism 200B causes the strings of the elastic member 7b' to swing at predetermined cycles in the cross direction CD. Accordingly, the elastic member 6b' is placed in a curved state between the second web 7B and the third web 7C, so that the back leg gather 6b is formed.

The upper press roll 130A and the lower press roll 130B press the second web 7B and the third web 7C, onto which the adhesive is applied, with the elastic members 6a' and 6b' being held between the second web 7B and the third web 7C. For this reason, the elastic members 6a' and 6b' are bonded between the second web 7B and the third web 7C in a state where the elastic members 6a' and 6b' are swung by the swing guide mechanism 120. Consequently, the large ring portion 6c is formed. On the other hand, even though the elastic members 6a' and 6b' are placed between the second web 7B and third web 7C, the elastic members 6a' and 6b' generate restoring force to form the small ring portion 6d because the adhesive is not applied to the center portion of the third web 7C.

The operation of the swing guide mechanism 120 is described in detail with reference to FIGS. 4 and 6. The first swing guide mechanism 200A and the second swing guide mechanism 200B are similarly controlled. Thus, the description is given by using the first swing guide mechanism 200A and the elastic member 6a' which is placed by the first swing guide mechanism 200A.

In FIG. 4, the swing guide mechanism 120 has the tip end portion 222 from which the elastic member 6a' is fed. The tip end portion 222 is alternately moved by the arm member 220 guiding the elastic member 6a' in a first direction Da extending from the center portion of the second web 7B (the third web 7C) being conveyed in the conveyance direction MD to a first end portion 7a in the cross direction CD and a second direction Db extending from the center portion of the second web 7B (the third web 7C) to a second end portion 7b opposite to the first end portion. In doing so, the elastic member 6a' is brought into contact with the second web 7B and the third web 7C in a way to be therebetween to form a gather waveform (a predetermined waveform).

In FIG. 4, the center line GL shows the center line of the gather waveform in the cross direction CD. In the embodiment, the cycle of the amplitude of the elastic member 6a' in the second direction Db on the web is shorter than that in the first direction Da when the center line GL is used as a reference.

The moving center ML of the tip end portion 222 is displaced toward the shorter cycle of amplitude, i.e. the second direction Db with respect to the center line GL.

In the embodiment, the tip end portion 222 constitutes a feeding part 300 and the swing guide mechanism 120 constitutes a guide unit 310. Also, the conveyance direction MD is a predetermined direction.

FIG. 6 is a schematic view for illustrating the elastic member 6a' which is placed on the web and the operation of the tip end portion 222 which places the elastic member 6a', in the top view (the view on arrow A in FIG. 3) shown in FIG. 4. The waveform shown in FIG. 6 shows the waveform of the elastic member 6a' placed between the second web 7B and the third web 7C, and also corresponds to the gather waveform of the front leg gather 6a shown in FIG. 4. The solid line portion W1 shows the waveform of the elastic member 6a' which have been already placed between the second web 7B and the third web 7C. The dashed line portion W2 shows the position at which the elastic member 6a' is supposed to be placed.

In the embodiment, in the plan view of the composite web 7, a nip point N1 is the position where the elastic member 6a' is brought into contact with the second web 7B and the third web 7C at time t1. The tip end portion 222 is at least in the feeding position P1 on a tangent line at the nip point N1. At this time, a distance between the tip end portion 222 (i.e. the feeding position P1) and the nip point N1 is expressed by a feeding distance LN1.

In general, when the tip end portion 222 is placed in the feeding position P1 on the tangent line to the gather waveform at the nip point N1, the elastic member 6a' can be placed along the gather waveform. However, in the embodiment, when the tip end portion 222 moves in the first direction Da, the tip end portion 222 is placed in a marginal position m1 which is positioned closer to the first end portion 7a than the feeding position P1 on the tangent line to the gather waveform at the nip point N1. Similarly, when the tip end portion 222 moves in the second direction Db, the tip end portion 222 is placed in a marginal position m2 which is positioned closer to the second end portion 7b than a feeding position (unillustrated) on a tangent line to the gather waveform at a nip point.

In FIG. 6, a nip point N2 is a position where the elastic member 6a' is brought into contact with the second web 7B and the third web 7C at time t2. The nip point moves in the conveyance direction MD by a distance MD1 from the position at time t1. Note that the direction shown by arrow MD1 shows the moving direction of the nip point and the tip end portion 222 (the feeding position) with respect to the second web 7B and the third web 7C. The tip end portion 222 is at least in the feeding position P2 on the tangent line to the gather waveform at the nip point N2.

At this time, an angle φ between the tangent line to the gather waveform at the nip point N2 and the conveyance direction MD becomes largest. In other words, the nip point N2 corresponds to an inflection point in the curved line showing the gather waveform. In the embodiment, when the nip point goes beyond the position where the angle between the conveyance direction MD and the tangent line to the gather waveform becomes largest (i.e. the nip point N2), a distance (a feeding distance LN2) between the tip end portion 222 and the nip point becomes largest.

In other words, when the nip point goes beyond the position where the angle between the conveyance direction MD and the tangent line to the gather waveform becomes largest (i.e. the nip point N2), the feeding distance LN2 is larger than the feeding distance LN1.

When moving in the first direction Da, the tip end portion 222 is placed in the marginal position m2 which is positioned closer to the first end portion 7a than the feeding position P2 on the tangent line to the gather waveform at the nip point N2. Similarly, when moving in the second direction Db, the tip end portion 222 is placed in the marginal position m1 which is positioned closer to the second end portion 7b than the feeding position (unillustrated) on the tangent line to the gather waveform at the nip point.

Moreover, in the embodiment, as the nip point moves from the position where the nip point is in a position where the tangent line to the gather waveform at the nip point and the conveyance direction MD becomes parallel with each other to the position where the angle between the tangent line and the conveyance direction MD becomes largest, a distance M between the position on the tangent line at the nip point and the marginal position becomes gradually larger. In other words, in FIG. 6, the marginal distance M1 is smaller than the marginal distance M2.

In contrast, as the nip point moves from the position where the angle between the tangent line to the gather waveform at the nip point and the conveyance direction MD becomes largest to the position where the tangent line and the conveyance direction MD are parallel with each other, the distance M between the position on the tangent line to the gather waveform at the nip point and the marginal position becomes gradually smaller (unillustrated).

In the embodiment, it is preferable that the trajectory of the moving tip end portion 222 be a curved line projected at least in the conveyance direction MD. Specifically, in the embodiment, the tip end portion 222 is placed in the arm having the pivot in a predetermined position with respect to the web (the gather waveform). In other words, the tip end portion depicts a circular-arc trajectory intersecting the conveyance direction MD.

Specifically, in the embodiment, the swing guide mechanism 120 is a so-called swing arm unit that includes the motor 210 having the pivot 211, the arm member 220 which guides the elastic member 6a' to a predetermined position in the cross direction CD between the second web 7B and the third web 7C, the pivot 211, and a base end portion 221 of the arm member 220.

The tip end portion 222 feeding the elastic member 6a' is provided on the tip end of the arm member 220. The arm member 220 is coupled to the motor 210 having the pivot 211. Accordingly, the feeding position P1 and the marginal position m1 at which the tip end portion 222 is positioned are placed on the arc taking the length of the arm member 220 as a radius of a circle centering the pivot 211 at time t1. Similarly, the feeding position P2 and the marginal position m2 are placed on the arc taking the length of the arm member 220 as a radius of a circle centering the pivot 211 at time t2.

In the present embodiment, as shown in FIG. 4, the cycle of the amplitude of the elastic member 6a' toward the second end portion 7b on the web is shorter than that toward the first end portion 7a on the web when the center line L in the cross direction CD of the gather waveform is used as a reference. Moreover, the moving center of the tip end portion 222 is displaced from the center line L to the curved portion of the shorter cycle of the amplitude.

Furthermore, it is preferable that a ratio W/L of the amplitude W of the elastic member 6a' in the first direction Da or the second direction Db on the composite web 7 to the length L of the arm member 220 be 0.25 to 0.70.

Also, in the embodiment, the waveform of the elastic member placed by the first swing guide mechanism 200A and the waveform of the elastic member placed by the second swing guide mechanism 200B are different from each other. Furthermore, the length of the arm member 220 provided in the first swing guide mechanism 200A and the length of the arm member 220 provided in the second swing guide mechanism 200B are different from each other.

As described above, in the embodiment, the absorbent article 1 is a wearing-type diaper, and portions of the gather waveform at which the angle between the conveyance direction MD and the tangent line to the gather waveform is largest correspond to the inguinal regions in the leg-surrounding regions of the diaper.

Specifically, as shown in FIG. 4, the gather waveform of the elastic member 6a' placed by the first swing guide mechanism 200A corresponds to the waveform of the front leg gather 6a. Each of the regions Sk shown in FIG. 4 is a portion where the angle between the conveyance direction MD and the tangent line to the gather waveform is largest and is fitted to the inguinal region of the wearer when the wearer wears the diaper.

According to the elastic member attaching apparatus 100, in the plan view of the composite web 7, the distance (the feeding distance) between the tip end portion 222 and the nip point in the cross direction CD becomes larger when the nip point goes beyond the position where the angle between the conveyance direction MD and the tangent line to the gather waveform becomes largest.

In other words, the tip end portions 222 is placed in a further position in the plan view of the composite web 7 when the nip point goes beyond the position where the angle between the conveyance direction MD and the tangent to the gather waveform becomes largest. The elastic member 6a' is stretched by the tip end portion 222 further than a predetermined position, and then, while contracting, comes close to the web and touches the web, thereby being easily placed in the gather waveform.

Thus, according to the elastic member attaching apparatus 100, the string-like elastic member 6a' can be easily placed along the predetermined gather waveform in a desired position on the web being conveyed at high speed without elaborate profile designing.

In general, when a elastic member is placed in a gather waveform on a web, it is not realistic in terms of device layout to bring a feeding position of a elastic member into contact with a nip point to align the nip point with the feeding position of a elastic member. Here, the nip point is that at which a elastic member and a web come in contact with each other. For this reason, a certain distance is provided between the nip point and the feeding position of the elastic member 6a'.

When the elastic member is to be accurately placed along the gather waveform, it is only needed that the feeding position of the elastic member 6 is at least placed on an extension of the tangent line to the gather waveform at the nip point.

In addition, if the distance from the feeding position of the elastic member to the nip point is large, a range within which the elastic member can be placed along the gather waveform is wide even though the feeding position is not accurately placed on the tangent line to the gather waveform at the nip point of the gather waveform.

In the plan view of the composite web 7, the elastic member attaching apparatus 100 can have a wider tolerance when the nip point goes beyond the position where the angle between the conveyance direction MD and the tangent line to the gather waveform becomes largest. The reason is that the distance between the feeding position of the elastic member and the nip point becomes larger.

Thus, according to the elastic member attaching apparatus 100, the string-like elastic member 6a' can be easily placed along the predetermined gather waveform in a desired position on the web being conveyed at high speed without elaborate profile designing.

In the elastic member attaching apparatus 100, when the tip end portion 222 which is the feeding position of the elastic member 6a' is moving in the first direction Da, the tip end portion 222 is placed in the marginal position m1 closer to the first end portion 7a than the tangent line to the gather waveform at the nip point of the gather waveform. Also, when the tip end portion 222 is moving in the second direction Db, the tip end portion 222 is placed in the marginal position closer to the second end portion 7b than the tangent line to the gather waveform at the nip point of the gather waveform.

Furthermore, as the nip point moves from the position where the tangent line and the conveyance direction MD becomes parallel with each other to the position where the angle between the tangent line and the conveyance direction MD becomes largest, the distance M between the position on the tangent line to the gather waveform at the nip point and the marginal position m1 becomes gradually larger. In contrast, as the nip point moves from the position where the angle between the tangent line and the conveyance direction MD becomes largest to the position where the tangent line and the conveyance direction MD becomes parallel with each other, the distance between the position on the tangent line to the gather waveform at the nip point and the marginal position m1 becomes gradually shorter.

As described above, in the elastic member attaching apparatus 100, the distance from the feeding position of the elastic member 6a' to the nip point can be larger in a vicinity of the position where the angle between the tangent line and the conveyance direction MD becomes largest. Accordingly, the elastic member attaching apparatus 100 can have a wider tolerance.

Thus, according to the elastic member attaching apparatus 100, the string-like elastic member 6a' can be easily placed along the predetermined gather waveform in a desired position on the web being conveyed at high speed without elaborate profile designing.

In the elastic member attaching apparatus 100, the cycle of the amplitude of the elastic member 6a' in the second direction Db on the web is shorter than that in the first direction Da when the center line GL in the cross direction CD of the gather waveform (the predetermined waveform) is used as a reference. In addition, the moving center ML of the tip end portion 222 is displaced from the center line GL toward the shorter cycle of amplitude, i.e. the second direction Db.

With this configuration, the difference between the moving distances of the tip end potion 222 in the first direction Da and the second direction Db can be reduced. As a result, the feeding position of the elastic member 6a' can follow the gather waveform more accurately.

In the embodiment, the trajectory of the moving tip end portion 222 is at least a curved line projected in the conveyance direction MD, so that the tip end portion 222 provided on the tip end of the arm member 220 moves on the curved line projected in the conveyance direction MD. For this reason, a difference is caused in the distance between the tip end portion 222 and the nip point not only in the cross direction CD but also in the conveyance direction MD. Thus, the distance from the feeding position of the elastic member 6a' to the nip point (the feeding distance) can be lengthened in the conveyance direction MD, so that the tolerance can be further widened.

Thus, the string-like elastic member 6a' can be easily placed along the predetermined gather waveform in a desired position on the web being conveyed at high speed without elaborate profile designing.

In the embodiment, the swing guide mechanism 120 has the motor 210 having the pivot 211, the arm member 220 which guides the elastic member 6' to a predetermined position in the cross direction CD between the second web 7B and the third web 7C, the pivot 211, and a base end portion 221 of the arm member 220.

As described above, when the arm member 220 rotates, the tip end portion 222 provided on the tip end of the arm member 220 depicts the circular-arc trajectory. For this reason, on the both sides of the circular-arc, a difference is caused in the distance between the feeding position and the nip point not only in the cross direction CD but also in the conveyance direction MD. Thus, the distance from the feeding position of the elastic member 6a' to the nip point (the feeding distance) can be lengthened in the conveyance direction MD, so that the tolerance can be further widened.

Accordingly, the string-like elastic member 6a' can be easily placed along the predetermined gather waveform in a desired position on the web being conveyed at high speed without elaborate profile designing.

In the embodiment, a value of the distance from the feeding position to the nip point (the feeding distance) can be properly set by setting the ratio W/L of the amplitude W of the elastic member in the first direction Da or the second direction Db on the web to the length L of the arm member 220 to be 0.25 to 0.70. Thus, the elastic member 6a' can be placed along the gather waveform without elaborate profile designing.

In the embodiment, the swing guide mechanism 120 includes a pair of the first swing guide mechanism 200A and the second swing guide mechanism 200B. The waveform of the elastic member 6a' formed by the first swing guide mechanism 200A is different from the waveform of the elastic member 6a' formed by the second swing guide mechanism 200B. In addition, the length of the arm member provided in the first swing guide mechanism 200A is different from the length of the arm member provided in the second swing guide mechanism 200B.

With this configuration, elastic members can be placed along different gather waveforms on one web conveyed in the conveyance direction MD at a conveyance velocity V1.

In the embodiment, the absorbent article 1 is a wearing-type diaper, and portions of the gather waveform at which the angle between the conveyance direction MD and the tangent line to the gather waveform becomes largest correspond to the inguinal regions in the leg-surrounding regions of the diaper. Whether or not the absorbent article 1 is comfortably fitted to the wearer is determined by the regions corresponding to the inguinal regions of the diaper. Thus, the regions are the most important portions.

The elastic member attaching apparatus 100 can extend the distance from the feeding position to the nip point when the elastic member 6a' is placed at the position where the angle between the tangent line and the conveyance direction MD becomes largest, i.e. the regions Sk corresponding to the inguinal regions. Thus, the tolerance can be widened.

Accordingly, the elastic member 6a' can be accurately placed at the position corresponding to the inguinal region which requires the highest precision, without elaborate profile designing.

Moreover, as shown in FIG. 7, in the elastic member attaching apparatus 100, the speed controller 105 maintains the feeding speed of the elastic member 6a' constituting the front leg gather 6a which is fed from the front gather feeding mechanism 103 and the feeding speed of the elastic member 6b' constituting the back leg-gather 6b which is fed from the back gather feeding mechanism 104 in a constant speed different from the conveyance velocity (V1) of the web.

With this configuration, the elastic members 6a' and 6b' are placed between the second web 7B and the third web 7C and are pressed by the press roll mechanism 130. At this time, the elastic members 6a' and 6b' are under tensile stress caused by the difference between the conveyance velocity and the feeding speed.

Provided that the feeding speed is constant, as the difference between the feeding distances LN1 and LN2 is larger, the difference between the tensile stress of the elastic member in the feeding position P1 and the tensile stress of the elastic member in the feeding position P2 becomes larger. When there is a difference in the tensile stress by position, the absorbent article is prevented from being comfortably fitted to the wearer.

The swing guide mechanism 120 is a swinging arm unit. As the distance between any point on the trajectory of the swinging tip end portion 222 and the nip point (N1 or N2) is larger, the difference between the feeding distances which is attributable to the positional difference of the tip end portion 222 on the trajectory (i.e. the difference between the feeding distances L1 and L2) becomes smaller.

Accordingly, it is preferable that the distance between any point on the trajectory of the swinging tip end portion 222 and the nip point (N1 or N2) be large. Accordingly to the elastic member attaching apparatus 100, the distance between the nip point (N1 or N2) and the feeding position of the elastic member 6a' or 6b' (i.e. the tip end portion 222) can be lengthened.

Accordingly, the elastic member 6a' constituting the front leg gather 6a and the elastic member 6b' constituting the back leg gather 6b can be placed between the second web 7B and the third web 7C with the tensile stress of the elastic members 6a' and 6b' being less changeable.

As described above, the details of the present invention have been disclosed through the embodiment of the present invention. It should not be understood that the description and drawings which constitute part of this disclosure limit the present invention. Based on this disclosure, those skilled in the art may easily come up with various alternative embodiments, examples and operation techniques.

For example, the embodiment of the present invention can be modified as follows. Specifically, the method of manufacturing an absorbent article and the elastic member attaching apparatus are applicable not only to an absorbent article 1 (or a so-called disposable diaper) including a front waistline region 10, a back waistline region 20, a crotch region 30 and the like, but also to various articles including disposable gowns for medical use and disposable wears for sports.

In addition, the description has been given of the case where the elastic member as a component constituting the absorbent article 1 is a stretchable string-like rubber or the like. However, the elastic member is not limited to this and may be a rubber such as a flat rubber or a sheet-like rubber.

Also, the elastic member is not necessarily a rubber and may be a recoverable or stretchable fabric such as polyester or polyurethane or another stretchable fabric other than these fabrics. Moreover, these fabrics may be twisted together to be used as the elastic member.

In addition, the description has been given of the case where the lengths of the arm members 220 of the first swing guide mechanism 200A and the second swing guide mechanism 200B are different from each other. However, the present invention is not limited to this configuration and the lengths may be equal.

In the embodiment, the first swing guide mechanism 200A and the second swing guide mechanism 200B are designed to have the arm members 220 whose movable areas partially overlap with each other. However, the arm members 220 may be arranged in a way that the movable areas of the arm members 220 do not overlap with each other. The distance between the first swing guide mechanism 200A and the second swing guide mechanism 200B in the width direction of the web is adjustable as needed according to the shapes of the absorbent article (or a disposable diaper). For example, the front leg gather 6a and the back leg gather 6b may be conveyed with a predetermined distance therebetween being kept.

In addition, the description has been given of the case where the program operating the motor 210 of the first swing guide mechanism 200A is different from the program operating the motor 210 of the second swing guide mechanism 200B. However, the present invention is not limited to this configuration, and these programs may be equal. In other words, the predetermined stretching magnification and layout of the front leg gather 6b may be equal to those of the back leg gather 6b.

Furthermore, the description has been given of the case where the tip end portion 222 of the arm member 220 has the insertion hole 223 into which the leg gather 6 is inserted. However, the present invention is not limited to this configuration, and is only needed to be designed to guide the leg gather 6. For example, a U-letter shape groove may be formed in the arm member 220.

In the embodiment, the description has been given of the case where the swing guide mechanism 120 includes the motor 210 having the pivot 211, the arm member 220 guiding the elastic member 6' to a predetermined position in the cross direction CD between the second web 7B and the third web 7C, the pivot 211, and the base end portion 221 of the arm member 220. However, the present invention is not limited to the configuration in which the arm member 220 swings about the pivot 211.

For example, the present invention may have a mechanism in which a guide unit having the feeding position of the elastic member 6a' is movable within the range regulated by a circular-arc slide rail, a circular-arc rib, a circular-arc cam groove, a cam follower, or the like. In this case, the examples of applicable driving means include a timing belt, a link, and a circular-arc linear servo.

As described above, the present invention naturally includes various embodiments which are not described herein. Accordingly, the technical scope of the present invention should be determined only by the matters to define the invention in the scope of claims regarded as appropriate based on the description.

The entire content of Japanese Patent Application 2009-048652 (filed on Mar. 2, 2009) is incorporated herein by reference.

INDUSTRIAL APPLICABILITY

Therefore, according to the present invention, it is possible to provide an apparatus and a method of manufacturing an absorbent article that are capable of placing a elastic member in a desired position on a web being conveyed at high speed without elaborate profile designing.

REFERENCE SIGNS LIST 1 absorbent article
2 top sheet
3 back sheet
4 absorber
5 waist gather
5a front waist gather
5b back waist gather
5', 5a', 5b' elastic member 6 leg gather
6a front leg gather
6b back leg gather
6c large ring portion
6d small ring portion
6', 6a', 6b' elastic member
7 composite web
7A first web
7B second web
7B' second web roll
7C third web
7C' third web roll
10 front waistline region
10A side edge
20 back waistline region
20A side edge
30 crotch region
40 joint portion
40A predetermined region
50 waist opening region
60 leg-surrounding openings
100 elastic member attaching apparatus
101 upper web feeding mechanism
102 lower web feeding mechanism
103 front gather feeding mechanism
104 back gather feeding mechanism
105 speed controller
110 adhesive applying mechanism
110A upper adhesive applying mechanism
110B lower adhesive applying mechanism
120, 120A swing guide mechanism (guide arm unit)
130 press roll mechanism
130A upper press roll
130B lower press roll
131A, 131B rotation axis
140A, 140B backup roll
150A, 150B feed roll
151A, 151B branch roll
200A first swing guide mechanism
200B second swing guide mechanism
210 motor
211 pivot
212 bracket
213 base plate
220, 220A arm member
221 base end portion
222 tip end portion

The invention claimed is:

1. An apparatus for manufacturing an absorbent article, the apparatus comprising:
 a guide unit that has a feeding part configured to feed an elastic member and that is configured to guide the elastic member, wherein the guide unit is configured to move the feeding part alternately in a first direction and a second direction, so that the elastic member is brought into contact with a web conveyed in a predetermined direction and is placed in a predetermined waveform, the first direction extending from a center portion of the web to a first end portion in a cross direction intersecting the predetermined direction, the second direction extending from the center portion to a second end portion opposite to the first end portion in the cross direction; and
 a speed controller configured to control a speed of the elastic member fed by the feeding part,
 wherein
 the speed controller is configured to maintain the speed of the elastic member at a constant speed different from a conveyance velocity of the web being conveyed in the predetermined direction, and
 in a plan view of the web, the guide unit is configured to control a position of the feeding part so that a distance between the feeding part and a nip point where the elastic member is brought into contact with the web becomes largest when the nip point goes beyond a position in the predetermined waveform where an angle between the predetermined direction and a tangent line to the predetermined waveform is largest,
 the guide unit is configured to move, when moving the feeding part in the first direction, the feeding part in a first marginal position closer to the first end portion than a first position on the tangent line to the predetermined waveform at the nip point,
 the guide unit is configured to move, when moving the feeding part in the second direction, the feeding part in a second marginal position closer to the second end portion than a second position on the tangent line to the predetermined waveform at the nip point, and
 the guide unit is configured to move the feeding part so that a distance between the first position on the tangent line to the predetermined waveform at the nip point and the first marginal position becomes gradually larger as the nip point moves from a position where the tangent line and the predetermined direction are parallel with each other toward the position where the angle between the tangent line and the predetermined direction is largest.

2. The apparatus according to claim 1, wherein
 the guide unit is configured to move the feeding part so that a distance between the second position on the tangent line to the predetermined waveform at the nip point and the second marginal position becomes gradually smaller as the nip point moves from the position where the angle between the tangent line and the predetermined direction becomes largest, toward the position where the tangent line and the predetermined direction are parallel with each other.

3. The apparatus according to claim 1, wherein the guide unit is configured to move the feeding part, so that
 any one of cycles of amplitude of the elastic member in the first direction and the second direction on the web is shorter than the other one of the cycles of amplitude when the center line of the predetermined waveform in the cross direction is used as a reference, and
 a moving center of the feeding part is displaced toward the shorter cycle of the amplitude with respect to the center line.

4. The apparatus according to claim 1, wherein the feeding part is movable along a curved line projected at least in the predetermined direction.

5. The apparatus according to claim 1, wherein the guide unit comprises:
 an arm member having an end portion defining the feeding part; and
 a motor having a shaft at a base end portion of the arm member and configured to swing the arm member in the cross direction at predetermined cycles.

6. The apparatus according to claim 5, wherein a ratio W/L of the amplitude W of the elastic member on the web in the first direction or the second direction to a length L of the arm member is from 0.25 to 0.70.

7. The apparatus according to claim 5, wherein
 the guide unit includes a pair of a first guide unit and a second guide unit configured such that a first waveform of the elastic member formed by the first guide unit is different from a second waveform of the elastic member formed by the second guide unit, and a length of the arm member provided in the first guide unit is different from a length of the arm member provided in the second guide unit.

8. The apparatus according to claim 1, wherein the absorbent article is a diaper, and the position on the predetermined waveform where the angle between the predetermined direction and the tangent line to the predetermined waveform is largest corresponds to an inguinal region in a leg-surrounding region of the diaper.

9. The apparatus according to claim 1, wherein the first position on the tangent line to the predetermined waveform at the nip point is an intersection of (i) the tangent to the predetermined waveform at the nip point and (ii) an arc defined by the feeding part, and the second position on the tangent line to the predetermined waveform at the nip point is the intersection of (i) the tangent to the predetermined waveform at the nip point and (ii) the arc defined by the feeding part.

10. The apparatus according to claim 1, wherein the guide unit further includes a servomotor configured to control a speed of the feeding part and the position of the feeding part.

11. The apparatus according to claim 10, wherein the speed controller is configured to control said servomotor of the guide unit.

12. An apparatus for manufacturing an absorbent article, said apparatus comprising:

a guide unit that has a feeding part configured to feed an elastic member and that is configured to guide the elastic member, wherein the guide unit is configured to move the feeding part alternately in a first direction and a second direction, so that the elastic member is brought into contact with a web conveyed in a predetermined direction and is placed in a predetermined waveform, the first direction extending from a center portion of the web to a first end portion in a cross direction intersecting the predetermined direction, the second direction extending from the center portion to a second end portion opposite to the first end portion in the cross direction; and a speed controller configured to control a speed of the elastic member fed by the feeding part, wherein the speed controller is configured to maintain the speed of the elastic member at a constant speed different from a conveyance velocity of the web being conveyed in the predetermined direction, the guide unit is configured to control a speed and a position of the feeding part, and in a planar view of the web, the guide unit is configured to control the speed and the position of the feeding part to move, when moving the feeding part in the first direction, the feeding part in a first marginal position located closer to the first end portion than an intersection of (i) the tangent to the predetermined waveform at the nip point and (ii) an arc defined by the feeding part, and the guide unit is configured to control the speed and the position of the feeding part to move, when moving the feeding part in the second direction, the feeding part in a second marginal position located closer to the second end portion than the intersection of (i) the tangent to the predetermined waveform at the nip point and (ii) the arc defined by the arm member.

13. The apparatus according to claim 12, wherein the guide unit further includes a servomotor configured to control the speed and the position of the feeding part.

14. The apparatus according to claim 13, wherein the speed controller is configured to control said servomotor of the guide unit.

* * * * *